US 9,301,839 B2

(12) United States Patent
Stante et al.

(10) Patent No.: US 9,301,839 B2
(45) Date of Patent: Apr. 5, 2016

(54) TRANSCATHETER PROSTHETIC HEART VALVE DELIVERY DEVICE WITH RELEASE FEATURES

(71) Applicant: Medtronic CV Luxembourg S.a.r.l., Luxembourg (LU)

(72) Inventors: Glenn Stante, Turlock, CA (US); Joshua Dwork, Santa Rose, CA (US); Donna Barrett, Galway (IE); Niall Duffy, Galway (IE); Hubert Yeung, Santa Rosa, CA (US); Adam Shipley, San Rafael, CA (US)

(73) Assignee: Medtronic CV Luxembourg S.a.r.l., Luxembourg (LU)

( * ) Notice: Subject to any disclaimer, the term of this patent is extended or adjusted under 35 U.S.C. 154(b) by 380 days.

(21) Appl. No.: 13/787,937

(22) Filed: Mar. 7, 2013

(65) Prior Publication Data
US 2013/0274855 A1  Oct. 17, 2013

Related U.S. Application Data

(60) Provisional application No. 61/625,509, filed on Apr. 17, 2012.

(51) Int. Cl.
A61F 2/24 (2006.01)
A61F 2/95 (2013.01)
A61F 2/962 (2013.01)
A61F 2/966 (2013.01)

(52) U.S. Cl.
CPC ............... *A61F 2/2436* (2013.01); *A61F 2/243* (2013.01); *A61F 2/2418* (2013.01); *A61F 2/95* (2013.01); *A61F 2/962* (2013.01); *A61F 2/966* (2013.01)

(58) Field of Classification Search
CPC ....... A61F 2/24; A61F 2/2412; A61F 2/2418; A61F 2/2466; A61F 2/95; A61F 2/962; A61F 2/966; A61F 2/2427; A61F 2/243; A61F 2/2436; A61F 2002/9665
See application file for complete search history.

(56) References Cited

U.S. PATENT DOCUMENTS

| 7,740,655 | B2 | 6/2010 | Birdsall |
| 8,414,645 | B2 | 4/2013 | Dwork et al. |
| 8,562,673 | B2 | 10/2013 | Yeung et al. |
| 8,852,271 | B2 * | 10/2014 | Murray et al. ............... 623/2.11 |
| 2006/0265056 | A1 | 11/2006 | Nguyen et al. |
| 2007/0239269 | A1 | 10/2007 | Dolan et al. |
| 2011/0264202 | A1 * | 10/2011 | Murray et al. ............... 623/2.11 |

* cited by examiner

Primary Examiner — Todd J Scherbel

(57) ABSTRACT

A delivery system for percutaneously delivering and deploying a stented prosthetic heart valve. The delivery device includes a delivery sheath slidably disposed over an inner shaft, and a capture assembly. The capture assembly includes at least one release feature for releasing the stented prosthetic heart valve from the delivery device.

14 Claims, 14 Drawing Sheets

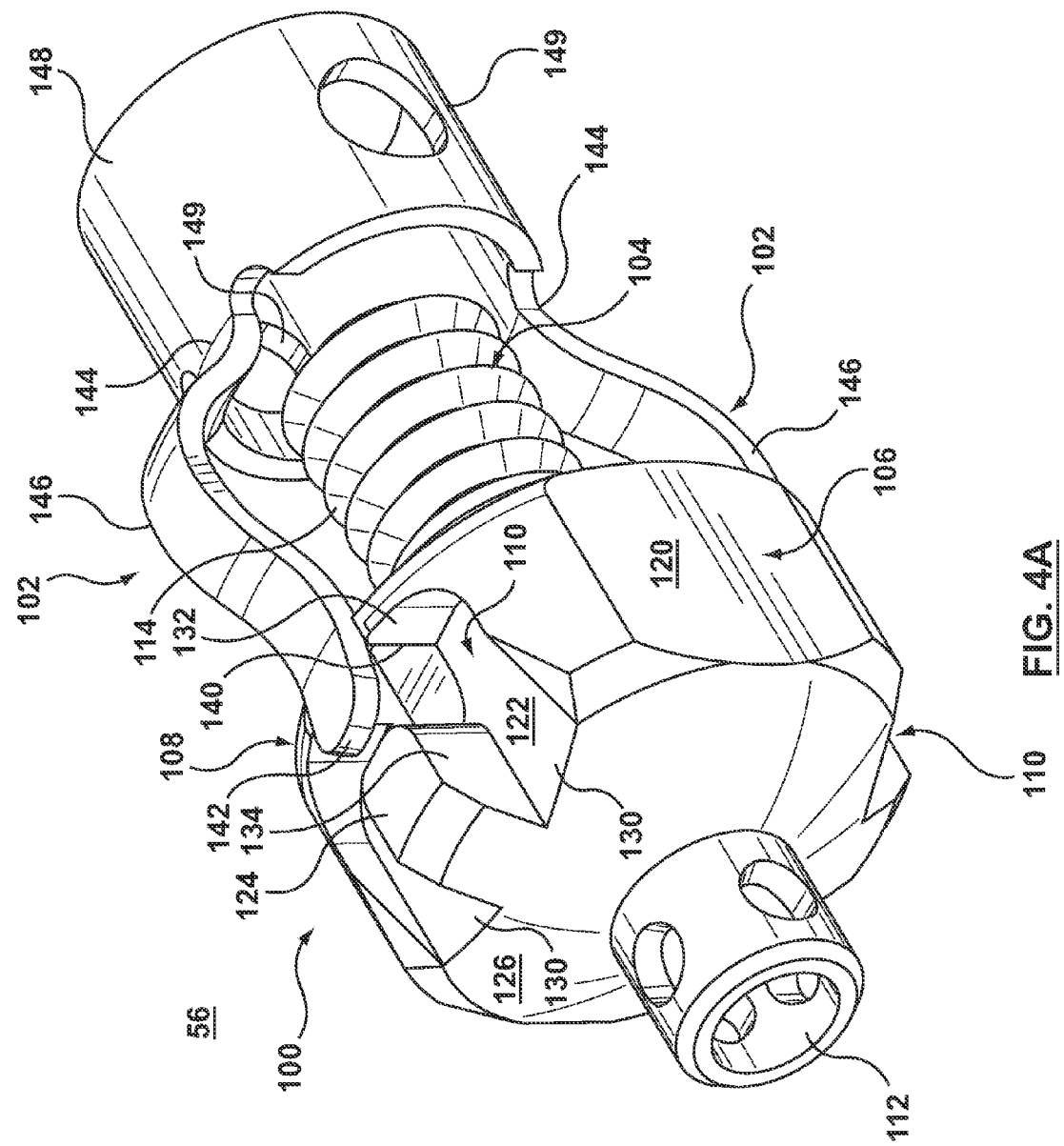

ated balloon catheter is slidably disposed within an outer delivery sheath. Once delivered to the implantation site, the balloon is inflated to deploy the prosthesis. With either of these types of percutaneous stented prosthetic valve delivery devices, conventional sewing of the prosthetic heart valve to the patient's native tissue is typically not necessary.

TRANSCATHETER PROSTHETIC HEART VALVE DELIVERY DEVICE WITH RELEASE FEATURES

CROSS-REFERENCE TO RELATED APPLICATION

This application claims priority under 35 U.S.C. §119(e) to U.S. Provisional Patent Application Ser. No. 61/625,509 filed on Apr. 17, 2012, and incorporated herein by reference.

BACKGROUND

The present disclosure relates to systems, devices, and methods for percutaneous implantation of a prosthetic heart valve. More particularly, it relates to delivery systems, devices, and methods for transcatheter implantation of a stented prosthetic heart valve.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available for percutaneous valve replacement procedures, and continue to be refined. The actual shape and configuration of any particular transcatheter prosthetic heart valve is dependent to some extent upon the native shape and size of the valve being replaced (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent is made of a self-expanding material and construction. With these devices, the valved stent is crimped down to a desired size and held in that compressed arrangement within an outer delivery sheath, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of catheter until it is as close to the diameter of the catheter as possible. The so- It is imperative that the stented prosthetic heart valve be accurately located relative to the native annulus immediately prior to full deployment from the catheter as successful implantation requires the prosthetic heart valve intimately lodge and seal against the native annulus. If the prosthesis is incorrectly positioned relative to the native annulus, serious complications can result as the deployed device can leak and may even dislodge from the native valve implantation site. As a point of reference, this same concern does not arise in the context of other vascular stents; with these procedures, if the target site is "missed," another stent is simply deployed to "make-up" the difference.

To carefully and safely deploy a transcatheter prosthetic heart valve, a clinician can employ imaging technology to evaluate the location of the prosthesis immediately prior to deployment. In particular, one desirable transcatheter prosthetic heart valve implantation technique entails partially deploying a distal region of the prosthesis from the delivery device and then evaluating a position of the deployed distal region relative to the native annulus. The clinician may further desire the ability to resheath or recapture the partially deployed region for subsequent repositioning of the prosthesis. Regardless, in the partially deployed state, the proximal region of the prosthetic heart valve must remain coupled to the delivery device. While, in theory, retaining a partially deployed prosthetic heart valve to the delivery device is straightforward, in actual practice the constraints presented by the stented prosthetic heart valve render the technique exceedingly difficult. In particular, the delivery device must not only securely retain the prosthetic heart valve in the partially deployed state, but also must consistently operate to release the prosthetic heart valve when full deployment is desired.

A stented heart valve is purposefully designed to rigidly resist collapsing forces once deployed so as to properly anchor itself in the anatomy of the heart. Thus, the delivery device component (e.g., outer delivery sheath) employed to retain the prosthesis in a collapsed arrangement must be capable of exerting a significant radial (inward) force. Conversely, this same delivery device component cannot be overly rigid so as to avoid damaging the transcatheter heart valve during deployment. Along these same lines, the aortic arch must be traversed with many percutaneous heart valve replacement procedures, necessitating that the delivery device provide sufficient articulation attributes. To meet these constraints, the outer delivery sheath typically incorporates a circumferentially rigid capsule, and a coupling structure is disposed within the delivery sheath for temporarily capturing the stented valve. While viable, conventional delivery device designs robustly engage the prosthetic heart valve within the capsule; this robust engagement facilitates the partial deployment technique described above, but the prosthetic heart valve may undesirably "catch" on the inner engagement structure when full deployment is intended and/or numerous, complex components are required to ensure complete deployment. Further, clinicians prefer that a significant portion of the prosthetic heart valve be exposed/expanded in the partially deployed state (e.g., the inflow region and at least a portion of the outflow region of the prosthesis). Unfortunately, existing delivery device designs cannot consistently meet this need.

In light of the above, a need exists for systems to restore (e.g., replace) a defective heart valve and corresponding stented transcatheter prosthetic heart valve delivery devices and methods that satisfy the constraints associated with percutaneous heart valve implantation and permit consistent partial and full deployment of the prosthesis.

SUMMARY

Some aspects in accordance with principles of the present disclosure relate to a delivery device for percutaneously deploying a stented prosthetic heart valve. The prosthetic heart valve has a stent frame to which a valve structure is attached. The delivery device includes a delivery sheath assembly, an inner shaft, and a capture assembly. The delivery sheath assembly terminates at a distal end and defines a lumen. The inner shaft is slidably disposed within the lumen. The capture assembly is configured to selectively couple the prosthetic heart valve relative to the inner shaft, and includes one or more release features to assist in releasing the stent frame from the inner shaft. The delivery device provides a delivery state in which the delivery sheath assembly retains the frame over the inner shaft. The delivery device further provides a deployment state in which the distal end of the delivery sheath assembly is withdrawn from over the prosthetic heart valve to permit the prosthetic heart valve to release from the inner shaft, including the one or more release features operating to release the stent frame from the delivery device.

BRIEF DESCRIPTION OF THE DRAWINGS

FIG. 4A is an enlarged, perspective view of a capture assembly portion of the delivery device of FIG. 3;

DETAILED DESCRIPTION

Figure 1A:
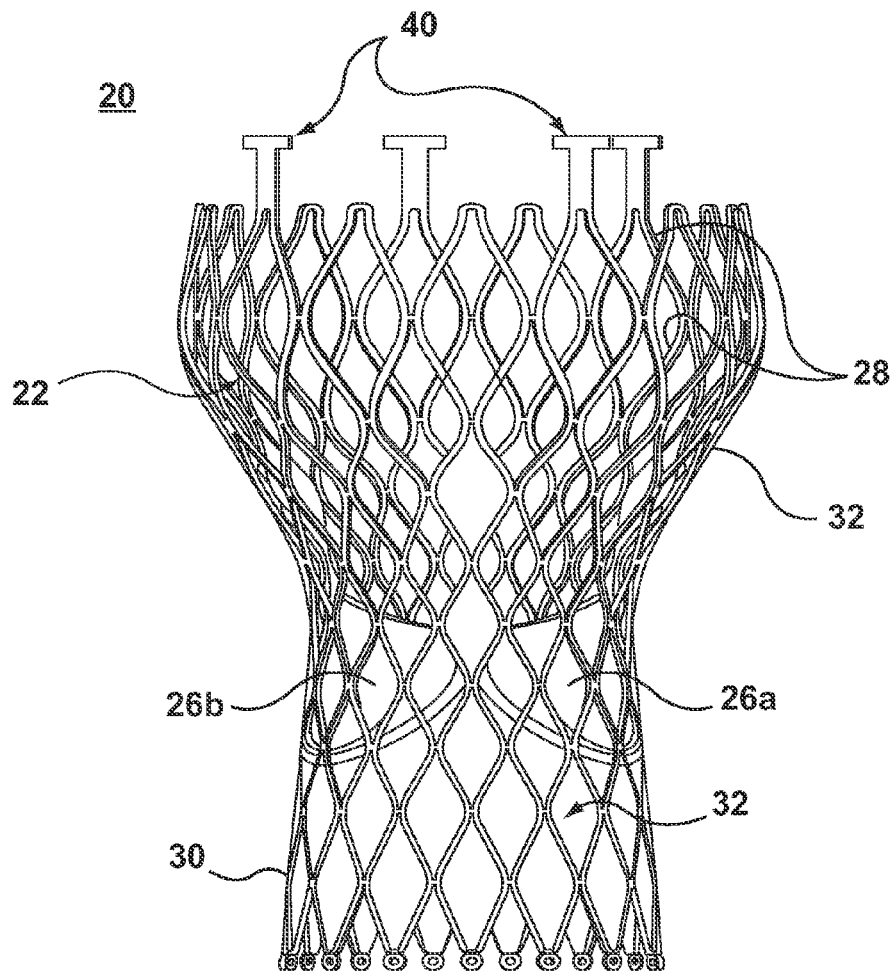
FIG. 1A is a side view of a stented prosthetic heart valve useful with systems, devices, and methods of the present disclosure and in a normal, expanded arrangement.

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from a compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached leaflets can be mounted onto a delivery device. The stent frame support structures are configured so that they can be changed to their normal, expanded arrangement when desired, such as by the relative movement of one or more sheaths relative to a length of the stent frame.

The wires of the stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 1B:
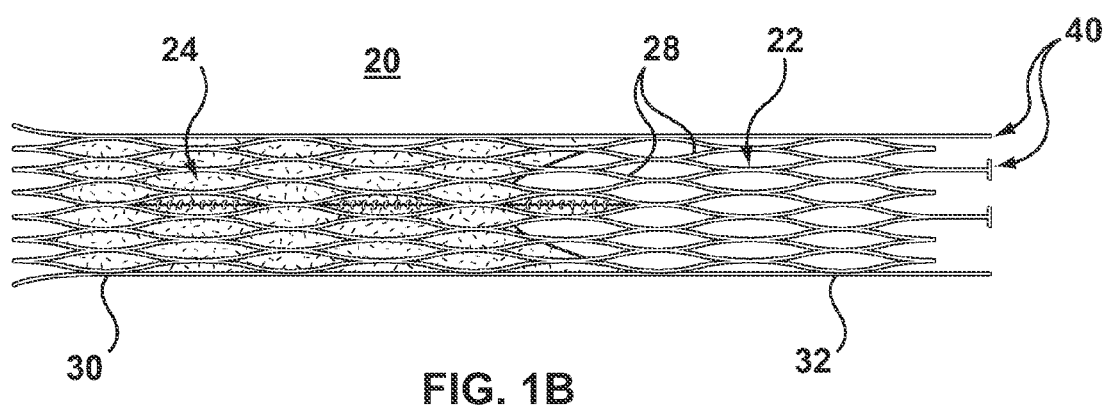
FIG. 1B is a side view of the prosthetic heart valve of FIG. 1A in a compressed arrangement.

With the above understanding in mind, one non-limiting example of a stented prosthetic heart valve 20 useful with systems and methods of the present disclosure is illustrated in FIG. 1A. As a point of reference, the prosthetic heart valve 20 is shown in a normal or expanded arrangement in the view of FIG. 1A; FIG. 1B illustrates the prosthetic heart valve 20 in a compressed arrangement (e.g., when compressively retained within an outer catheter or sheath (not shown)). The prosthetic heart valve 20 includes a stent or stent frame 22 and a valve structure 24. The stent frame 22 can assume any of the forms described above, and is generally constructed so as to be self-expandable from the compressed arrangement (FIG. 1B) to the normal, expanded arrangement (FIG. 1A). In other embodiments, the stent frame 22 is expandable to the expanded arrangement by a separate device (e.g., a balloon internally located within the stent frame 22). The valve structure 24 is assembled to the stent frame 22 and provides two or more (typically three) leaflets 26a, 26b. The valve structure 24 can assume any of the forms described above, and can be assembled to the stent frame 22 in various manners, such as by sewing the valve structure 24 to one or more of the wire segments 28 defined by the stent frame 22.

With the but one acceptable construction of FIGS. 1A and 1B, the prosthetic heart valve 20 is configured for replacing an aortic valve. Alternatively, other shapes are also envisioned, adapted for the specific anatomy of the valve to be replaced (e.g., stented prosthetic heart valves in accordance with the present disclosure can alternatively be shaped and/or sized for replacing a native mitral, pulmonic, or tricuspid valve). Regardless, the valve structure 24 can be arranged to extend less than an entire length of the stent frame 22. In particular, the valve structure 24 can be assembled to, and extend along, an inflow region 30 of the prosthetic heart valve 20, whereas an outflow region 32 is free of the valve structure 24 material. The terms "inflow" and "outflow" are in reference to an arrangement of the prosthetic heart valve 20 upon final implantation relative to the native aortic valve (or other valve) being replaced A wide variety of other constructions are also acceptable and within the scope of the present disclosure. For example, the valve structure 24 can be sized and shaped to extend along an entirety, or a near entirety, of a length of the stent frame 22. With embodiments in which the prosthetic heart valve 20 is to be implanted via a retrograde approach, the prosthetic heart valve 20 will be arranged within the corresponding delivery device such that the inflow region 30 is distal the outflow region 32. Thus, the inflow region 30 can alternatively be referenced as the distal region of the prosthetic heart valve 20, whereas the outflow region 32 serves as the proximal region. With these conventions in mind, a proximal end 36 of the stent frame 22 forms, in some embodiments, a plurality of posts 40. The posts 40 are defined at an intersection of two (or more) adjacent ones of the wire segments 28, and are circumferentially spaced about a circumference defined by the stent frame 22. While the stent frame 22 is shown in FIGS. 1A and 1B as having four of the posts 40, any other number, either greater or lesser, is equally acceptable. For example, the stent frame 22 can include as few as a single one of the posts 40.

Figure 2A:
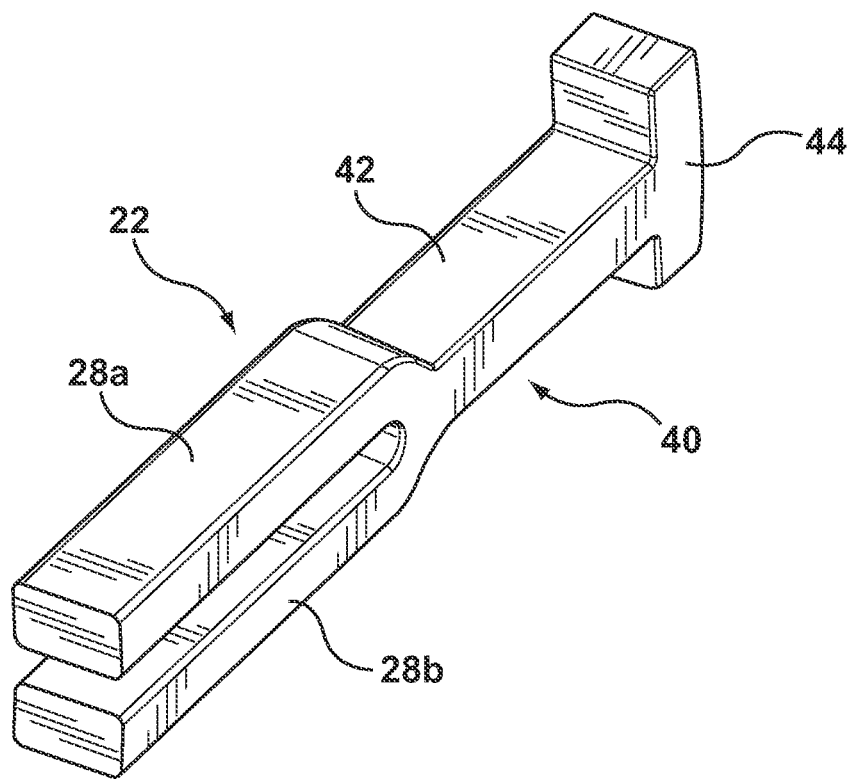
FIGS. 2A and 2B are enlarged, perspective views of alternative post portions usable with the prosthetic heart valve of FIGS. 1A and 1B.
Figure 2B:
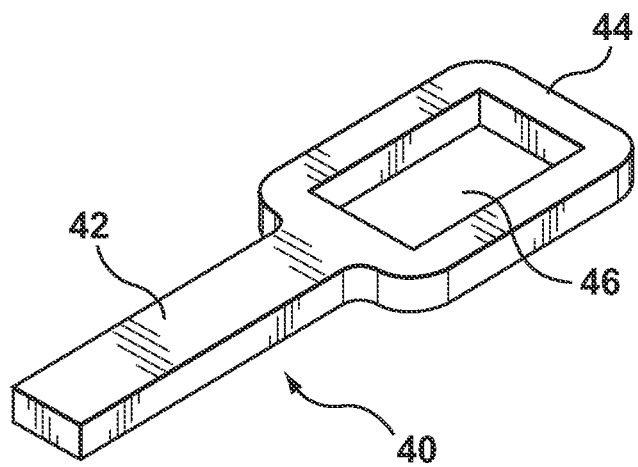

The posts 40 can assume various forms, and in some embodiments are identical. FIGS. 2A and 2B illustrate alternative constructions of the post 40 contemplated by the present disclosure in greater detail. As a point of reference, in the view of FIG. 2A, each post 40 includes two of the wire segments 28a, 28b, illustrated as intersecting at the post 40, with the post 40 projecting proximally from the wire segments 28a, 28b; a remainder of the stent frame 22 is omitted from each view for ease of explanation. The post 40 includes a shoulder 42 and a head 44. With respect to an orientation of the post 40 relative to the circumference defined by the stent frame 22 (FIG. 1A), the shoulder 42 and the head 44 can be described as having or defining a circumferential width, with the circumferential width of the head 44 being greater than that of the shoulder 42 for reasons made clear below. With some constructions, then, the post 40 can have a T-like shape. Moreover, as illustrated in FIG. 2B, the head 44 may include an aperture 46, wherein the head 44 can assume a larger overall profile as compared to the head 44 of FIG. 2A. A variety of other shapes are also acceptable. These and other features of the post 40, as well as the stent frame 22 as a whole, are described below in the context of loading to, and releasing from, a delivery device.

Figure 3:
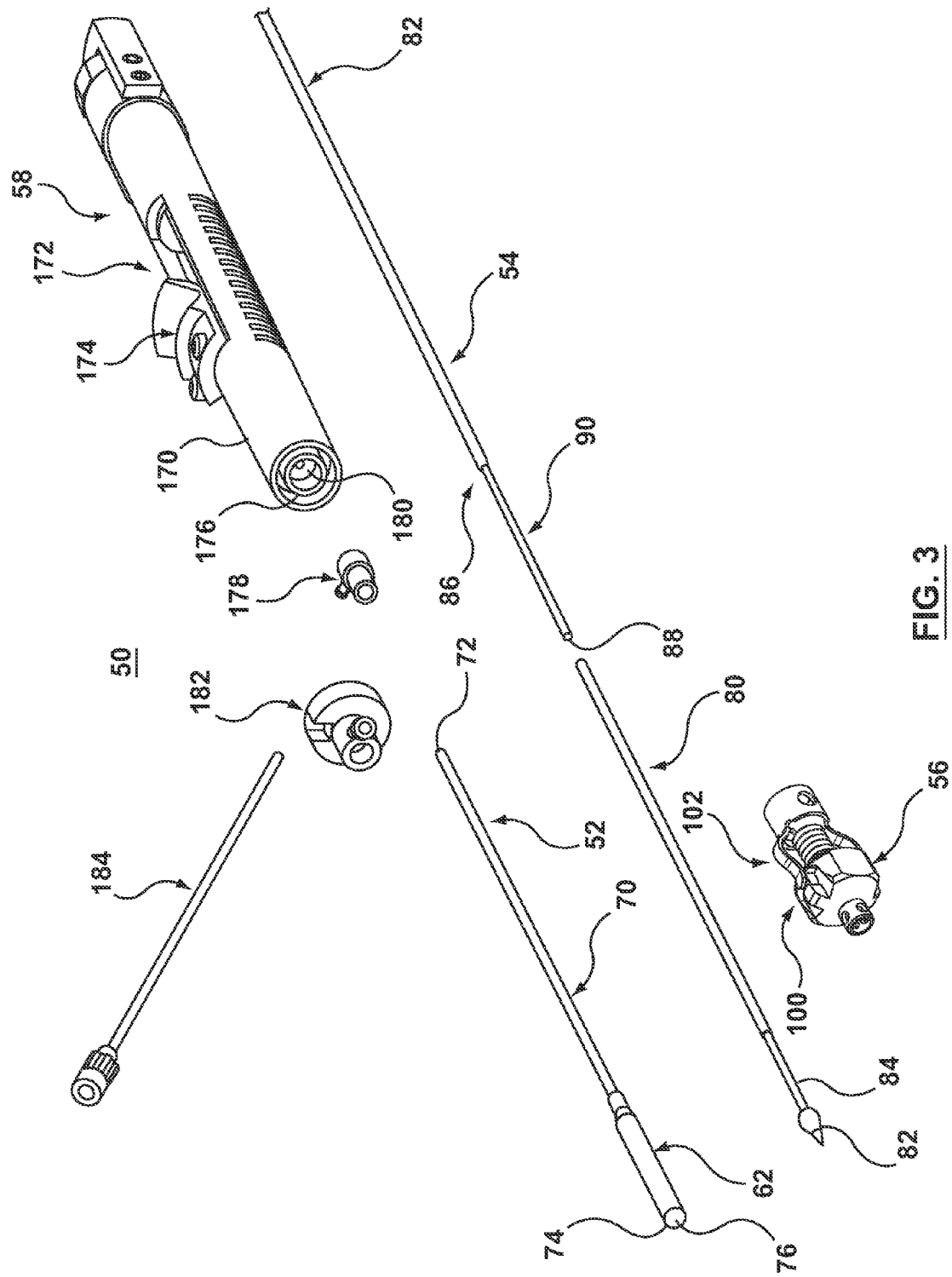
FIG. 3 is an exploded, perspective view of a stented prosthetic heart valve delivery device in accordance with principles of the present disclosure.

With the above understanding of the prosthetic heart valve 20 in mind, one embodiment of a transcatheter stented prosthetic heart valve delivery device 50 in accordance with principles of the present disclosure is shown in FIG. 3. The delivery device 50 includes a delivery sheath assembly 52, an inner shaft assembly 54, a capture assembly 56, and a handle 58. Other optional components, such as various release features, can also be included. Details on the various components are provided below. In general terms, however, the delivery device 50 combines with a stented prosthetic heart valve (not shown) to form a system for restoring (e.g., replacing) a defective heart valve of a patient. The delivery device 50 provides a delivery state in which the stented prosthetic heart valve is coupled to the inner shaft assembly 54 via the capture assembly 56, and compressively retained within a capsule 62 of the delivery sheath assembly 52. The delivery sheath assembly 52 can be manipulated to withdraw the capsule 62 proximally from the prosthetic heart valve via operation of the handle 58 in defining a deployment state of the delivery device 50, permitting the prosthesis to self-expand (alternatively, be caused to expand) and release from the inner shaft assembly 54 and the capture assembly 56. Other features discussed below, where provided, can operate to effectuate this release. Further, the handle 58 can be operated to maneuver the capsule 62 to effectuate a partial deployment state in which a distal region of the prosthetic heart valve is permitted to self-expand, whereas a proximal region of the prosthesis remains coupled to the capture assembly 56.

Various features of the components 52-58 reflected in FIG. 3 and described below can be modified or replaced with differing structures and/or mechanisms. Thus, the present disclosure is in no way limited to the delivery sheath assembly 52, the inner shaft assembly 54, the capture assembly 56, the handle 58, etc., as shown and described below. For example, the delivery device 50 can have any of the constructions described in U.S. application Ser. No. 12/870,567 filed Aug.

27, 2010 entitled "Transcatheter Valve Delivery Systems and Methods" and Ser. No. 12/886,975 filed Sep. 21, 2010 and entitled "Stented Transcatheter Prosthetic Heart Valve Delivery System and Method"; the teachings of which are incorporated herein by reference. More generally, delivery devices in accordance with the present disclosure provide features capable of compressively retaining a self-deploying, stented prosthetic heart valve (e.g., the capsule 62 in combination with the capture assembly 56), and a mechanism capable of effectuating partial and full release or deployment of the prosthesis (e.g., retracting the capsule 62 alone or in combination with the optional release features.

In some embodiments, the delivery sheath assembly 52 includes the capsule 62 and a shaft 70, and defines proximal and distal ends 72, 74. A lumen 76 (referenced generally) is formed by the delivery sheath assembly 52, extending from the distal end 74 through the capsule 62 and at least a portion of the shaft 70. The lumen 76 can be open at the proximal end 72. The capsule 62 extends distally from the shaft 70, and in some embodiments has a more stiffened construction (as compared to a stiffness of the shaft 70) that exhibits sufficient radial or circumferential rigidity to overtly resist the expected expansive forces of the stented prosthetic heart valve (not shown) when compressed within the capsule 62. For example, the shaft 70 can be a polymer tube embedded with a metal braiding, whereas the capsule 62 includes a laser-cut metal tube that is optionally embedded within a polymer covering. Alternatively, the capsule 62 and the shaft 70 can have a more uniform construction (e.g., a continuous polymer tube). Regardless, the capsule 62 is constructed to compressively retain the stented prosthetic heart valve at a predetermined diameter when loaded within the capsule 62, and the shaft 70 serves to connect the capsule 62 with the handle 58. The shaft 70 (as well as the capsule 62) is constructed to be sufficiently flexible for passage through a patient's vasculature, yet exhibits sufficient longitudinal rigidity to effectuate desired axial movement of the capsule 62. In other words, proximal retraction of the shaft 70 is directly transferred to the capsule 62 and causes a corresponding proximal retraction of the capsule 62. In other embodiments, the shaft 70 is further configured to transmit a user-generated rotational force or movement onto the capsule 62.

The inner shaft assembly 54 can have various constructions appropriate for supporting a stented prosthetic heart valve within the capsule 62. In some embodiments, the inner shaft assembly 54 includes an inner support shaft 80 and a tip 82. The inner support shaft 80 is sized to be slidably received within the lumen 76 of the delivery sheath assembly 52, and is configured for mounting of the capture assembly 56 and optional release features as desired. The inner support shaft 80 can include a distal segment 84 and a proximal segment 86. The distal segment 84 connects the tip 82 to the proximal segment 86, with the proximal segment 86, in turn, coupling the inner shaft assembly 54 to the handle 58. The components 80-86 can combine to define a continuous lumen 88 (referenced generally) sized to slidably receive an auxiliary component such as a guide wire (not shown).

The distal segment 84 can be a flexible polymer tube embedded with a metal braid. Other constructions are also acceptable so long as the distal segment 84 exhibits sufficient structural integrity to support a loaded, compressed stented prosthetic heart valve (not shown), as well as the capture assembly 56 and any optional release features mounted thereto. The proximal segment 86 can include, in some constructions, a leading portion 90 and a trailing portion 92. The leading portion 90 serves as a transition between the distal and proximal segments 84, 86, and thus in some embodiments is a flexible polymer tubing (e.g., PEEK) having an outer diameter slightly less than that of the distal segment 84. The trailing portion 92 has a more rigid construction (e.g., a metal hypotube), adapted for robust assembly with the handle 58. Other materials and constructions are also envisioned. For example, in alternative embodiments, the distal and proximal segments 84, 86 are integrally formed as a single, homogenous tube or solid shaft.

The tip 82 forms or defines a nose cone having a distally tapering outer surface adapted to promote atraumatic contact with bodily tissue. The tip 82 can be fixed or slidable relative to the inner support shaft 80.

The capture assembly 56 serves to selectively couple corresponding features of the stented prosthetic heart valve (not shown) relative to the inner shaft assembly 54, and can be configured for mounting to the inner support shaft 80. One embodiment of an exemplary embodiment of a capture assembly 56 is shown in greater detail in FIGS. 4A and 4B, and includes a spindle 100 and at least one biasing member 102. Other, alternative capture assemblies are further described herein and useful with the delivery device 50 of FIG. 3, as discussed in further detail below.

Figure 4B:
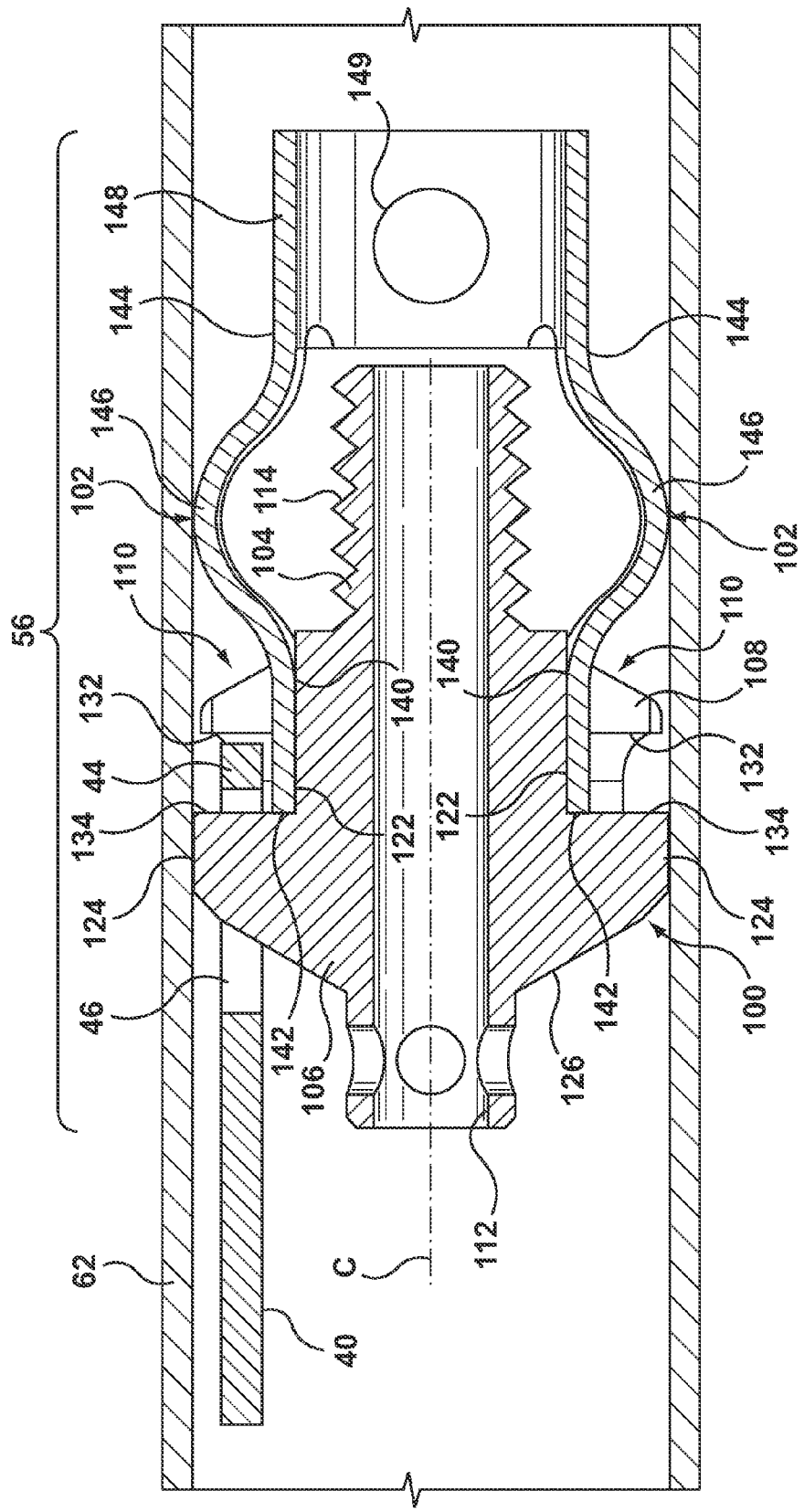
FIG. 4B is a cross-sectional view of the capture assembly of FIG. 4A assembled to a portion of an inner shaft component of the delivery device of FIG. 3.

The spindle 100 can assume various forms, and in some constructions includes a tubular base 104 and a hub 106 defining a flange 108 and at least one coupling section 110. The hub 106 radially projects from the tubular base 104, with the coupling section 110 forming one or more features configured to selectively engage the post(s) 40 (one of which is illustrated in FIG. 4B) of the stented prosthetic heart valve 20 (FIG. 1B) as described below. In the particular illustrated embodiment of FIGS. 4A and 4B, the coupling sections 110 are configured to engage the post 40 illustrated in FIG. 2B (e.g., including aperture 46), but can be modified so as to be configured to engage post 40 illustrated in FIG. 2A.

The tubular base 104 is configured to facilitate mounting of the spindle 100 to the inner support shaft 80 (FIG. 3), and defines a central passageway or lumen 112 and a proximal attachment section 114. The proximal section 114 is formed or defined proximal the flange 108 and can be configured for attachment to the inner support shaft 80, for example by forming outer ribs as shown. Other mounting techniques are also acceptable, such as the proximal section 114 being sized to coaxially receive the inner support shaft 80 or including a stepped diameter shoulder. Similarly, the lumen 112 can be sized to co-axially receive the distal segment 84 (FIG. 3) of the inner support shaft 80 for mounting thereto.

The hub 106 projects radially outwardly from the tubular base 104 to define an outer surface 120 and a u-shaped recess 122 forming part of the coupling section 110. The outer surface 120 includes or defines a projection 124 and a leading portion 126. The projection 124 extends from the recess 122 with the leading portion 126 tapering in diameter in distal extension from the projection 124. In other embodiments, the leading portion 126 can have a more uniform diameter in extension from the projection 124. Regardless, the recess 122 and projection 124 are sized to receive a post 40, in particular head 44 having aperture 46 (FIG. 4B). The recess 122 and projection 124 collectively define the coupling section 110. The hub 106 can form or define further coupling sections commensurate with the number of the posts 40 (FIG. 1A) provided with the prosthetic heart valve 20 (FIG. 1A). The plurality of coupling sections 110 can be identical and equidistantly spaced about a circumference of the hub 106 (e.g., spaced apart by 180° around a circumference of hub 106). Alternatively, only a single one of the coupling sections 110 need be provided. A width of each of the slots 130 of coupling sections 110 corresponds with a width of the post head 44

(FIG. 2B), with the projection 124 sized to receive the aperture 46 (FIG. 2B). The various interior surfaces defining the coupling section 110 are relatively smooth to facilitate sliding of the post 40 relative thereto.

The flange 108 is proximally spaced from the projection 124, and radially projects from the tubular base 104. With this spacing, then, the recess 122 of the coupling section 110 provides a recessed surface interposed between the projection 124 and the flange 108, with a surface of the recess 122 forming corresponding slots 130 positioned on either side of the projection 124. The outer diameter of the flange 108 can be approximately the maximum outer diameter of the projection 124 for reasons made clear below. Regardless, the flange 108 combines with the hub and the coupling section 110 to create the recess 122 configured to selectively receive the post head 44 as described below. Stated otherwise, the recess 122 is bounded by a U-shaped side wall 132 of the flange 108 facing the projection 124 and a U-shaped side wall 134 facing the flange 108.

The flange 108 can form or define at least one longitudinally-extending clearance slot 140. In some embodiments, a plurality of the clearance slots 140 are formed, with the number and arrangement of the clearance slots 140 corresponding with the number and arrangement of the coupling sections 110 in the hub 106 (e.g., respective ones of the clearance slots 140 are longitudinally aligned with corresponding ones of the coupling sections 110). The clearance slots 140 in the flange 108 are open to the recess 122, and may or may not have a circumferential width commensurate with the circumferential width of the recess 122. More generally, the clearance slots 140 in the flange 108 are sized and shaped to permit deflection of the biasing member(s) 102 as described below. In other embodiments, the flange 108 can be omitted.

The spindle 100 can be integrally formed as a homogenous part in some embodiments. In other constructions, one or more of the hub 106 and/or the flange 108 can be separately manufactured and subsequently assembled to the tubular base 104. Alternatively, the hub 106 and/or the flange 108 can be directly mounted onto the inner support shaft 80. Regardless, the spindle 100 is constructed of a relatively rigid material able to maintain a structural integrity of the spindle 100 in supporting the prosthetic heart valve 20 (FIG. 1A) in the compressed arrangement.

The biasing member 102 can be disposed within one of the recesses 122 in the hub 106, and is configured to self-transition from a deflected condition (illustrated in FIG. 4B) to a normal condition (illustrated in FIG. 4A). In some constructions, a plurality of the biasing members 102 are provided, with individual ones of the biasing members 102 being disposed within corresponding ones of the clearance slots 140. In some embodiments, the biasing members 102 are leaf spring-like bodies, defining a free end 142, a fixed end 144, and an intermediate region 146. With this construction, the leaf spring biasing member 102 has a shape memory characteristic (e.g., the leaf spring biasing member 102 can be formed from a metal alloy (such as Nitinol™ or stainless steel), or a polymer having shape memory attributes) that imparts an outwardly rotation of the free end 142 and the intermediate region 146 in the natural condition of FIG. 4A.

The biasing members 102 can be laser cut from a metal alloy and exposed to heat to form a desired shape. In the embodiment illustrated, the intermediate region extends outwardly in a curved or arcuate manner from the fixed end 144 and curves inwardly toward the free end 142, forming a hump that is substantially 'U' shaped in cross section. Free end 142 is formed to be substantially planar so as to lay flat against recess 122 when positioned in slot 140. Free end 142 can be polished or otherwise processed so as to produce a smooth finish to prevent damage to components of valve 20 and/or delivery system 30.

As shown in FIG. 4B, the leaf spring biasing member 102, can be deflected such that the free end 142 is positioned within the recess 122 (i.e., the deflected condition) via an externally applied force (i.e. applied by the capsule 62), and then self-revert or self-transition back to the normal condition upon removal of the external force. In particular, FIG. 4B illustrates the deflected condition of the biasing member 102, with each free end 142 rotated about its corresponding fixed end 144 and positioned within a corresponding recess 122. Relative to a central axis C of the tubular base 104 (and thus of the inner support shaft 80), a radially-outward projection of the free end 142 in the normal condition is greater than the radial projection in the deflected condition. In other words, relative to the central axis C, the free end 142 of the biasing member 102 in the normal condition extends radially beyond a radial extension of the free end 142 of the biasing member 102 in the deflected condition. In both the normal condition and the deflected condition, the intermediate region 146 radially projects to a greater distance from axis C than the fixed end 144.

The leaf spring biasing member 102 is sized for placement and deflection within a corresponding one of the clearance slots 140. Thus, a width of the biasing member 102 corresponds with (e.g., is slightly less than) a width of the corresponding clearance slot 140. Further, a shape of the intermediate region 146 in the normal condition is such that upon assembly of the biasing member within the capsule 62, the intermediate region 146 is compressed to the deflected condition.

Assembly of the biasing member(s) 102 to the spindle 100 can assume various forms. For example, in one embodiment in which a plurality of the biasing members 102 are provided, a ring 148 can be formed that interconnects the fixed end 144 of each of the biasing members 102. The ring 148 is then mounted to the inner support shaft 80 (e.g., adhesive, welding, etc.). In one embodiment, the ring 148 includes a plurality of apertures 149 adapted to receive a suitable adhesive for mounting ring 148 to the shaft 80. With this but one acceptable construction, then, each of the biasing members 102 longitudinally projects through a corresponding one of the clearance slots 140 in the flange 108, and into the corresponding one of the coupling sections 110. The free end 142 of each of the biasing members 102 is not directly attached to the spindle 100. Thus, in transitioning from the deflected condition to the normal condition, the free end 142 moves radially. Alternatively, the ring 148 can be omitted and the fixed end(s) 144 directly attached to the spindle 100. Further, while the fixed end 144 has been described as being arranged proximal the flange 108, in other constructions, the fixed end 144 is attached to the spindle 100 within or distal the corresponding coupling section 110 such that the free end 142 is proximal the fixed end 144.

While the biasing members 102 have been described as being leaf spring-like bodies, other constructions are also acceptable. For example, the biasing members 102 can be helical springs, linkages, elastically deformable bodies, etc., capable of positioning within at least a portion of the corresponding coupling section 110 and ejecting the stent post 40 (FIGS. 2A and 2B) from engagement within the coupling section 110 in self-transitioning from a deflected condition to a normal condition (otherwise having an increased radial projection relative to the central axis C of the inner support shaft 80) upon retracting capsule 62 by operation of handle 58.

Returning to FIG. 3, the handle 58 generally includes a housing 170 and an actuator mechanism 172 (referenced generally). The housing 170 maintains the actuator mechanism 172, with the actuator mechanism 172 configured to facilitate sliding movement of the delivery sheath assembly 52 (along with capsule 62) relative to the inner shaft assembly 54. The housing 170 can have any shape or size appropriate for convenient handling by a user. In one simplified construction, the actuator mechanism 172 includes a user interface or actuator 174 slidably retained by the housing 170 and coupled to a sheath connector body 176. The proximal end 72 of the delivery sheath assembly 52 is coupled to the sheath connector body 176 (e.g., via an optional mounting boss 178 in some embodiments). The inner shaft assembly 54, and in particular the proximal tube 86, is slidably received within a passage 180 of the sheath connector body 176, and is rigidly coupled to the housing 170. Sliding of the actuator 174 relative to the housing 170 thus causes the delivery sheath assembly 52 to move or slide relative to the inner shaft assembly 54 and the capture assembly 56, for example to effectuate deployment of a prosthesis from the inner shaft assembly 54. Alternatively, the actuator mechanism 172 can assume a variety of other forms differing from those implicated by the illustration of FIG. 3. Similarly, the handle 58 can incorporate other features, such as a cap 182 and/or a fluid port assembly 184.

Returning to FIG. 4B, the posts 40 (one of which is shown) are assembled to the spindle 100 at the coupling sections 110 such that the posts 40 cover biasing members 102 positioned in corresponding recesses 122. In particular, the stent frame 22 is crimped so as to have the posts 40 be coupled with the coupling sections 110. Additionally, the capsule 62 forces the biasing members 102 to the deflected condition and then the capsule 62 and frame 22 are positioned for delivery to a target site. Once positioned, the capsule 62 is retracted and, once retracted beyond the intermediate region 146 of the biasing member 102, the biasing member returns to the normal condition, In turn forcing the post 40 out of the coupling section 110, ultimately releasing the stent frame 22 from the spindle 100.

Figure 5A:
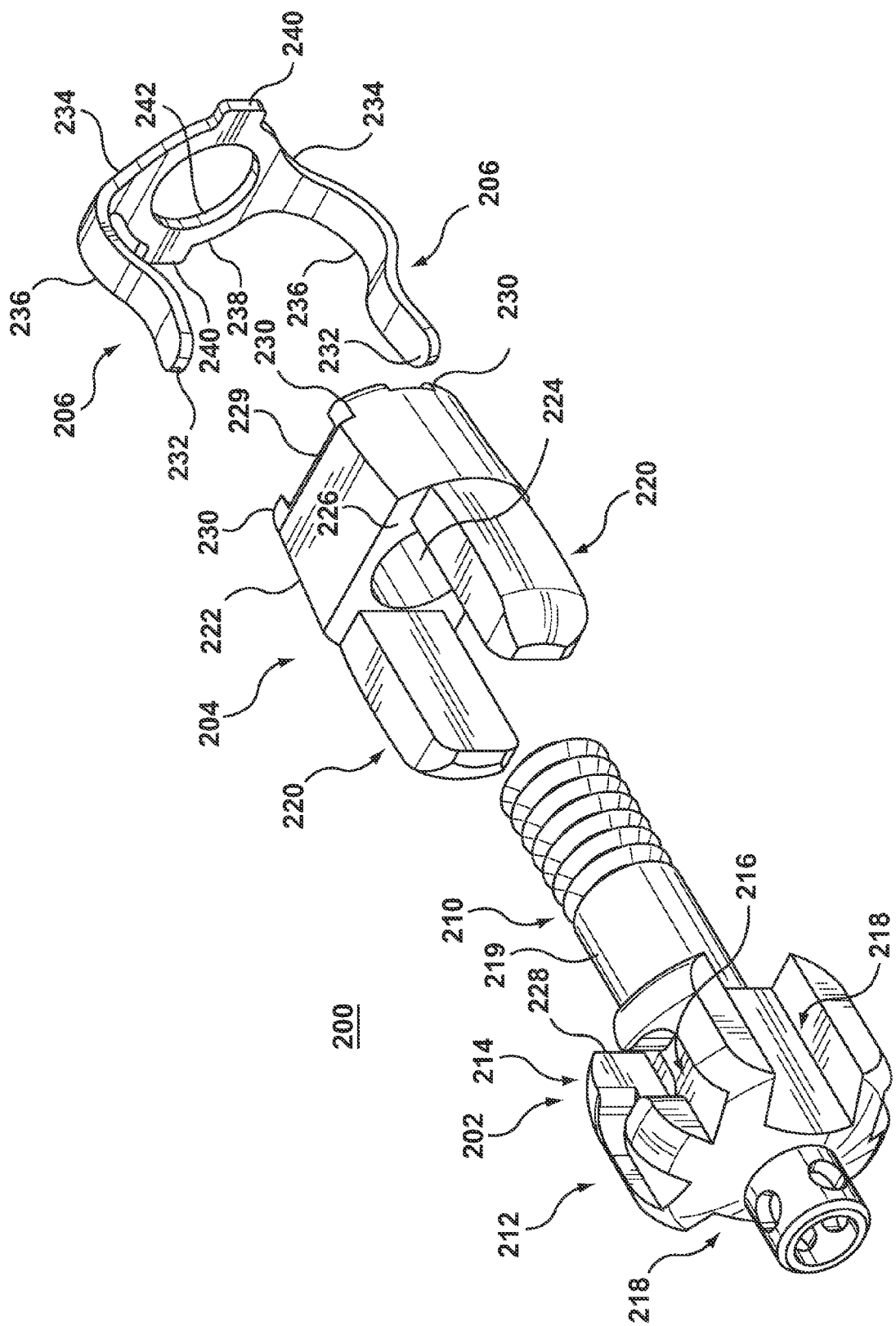
FIGS. 5A and 5B are enlarged, perspective views of an alternative capture assembly useful with the delivery device of FIG. 3.
Figure 5B:
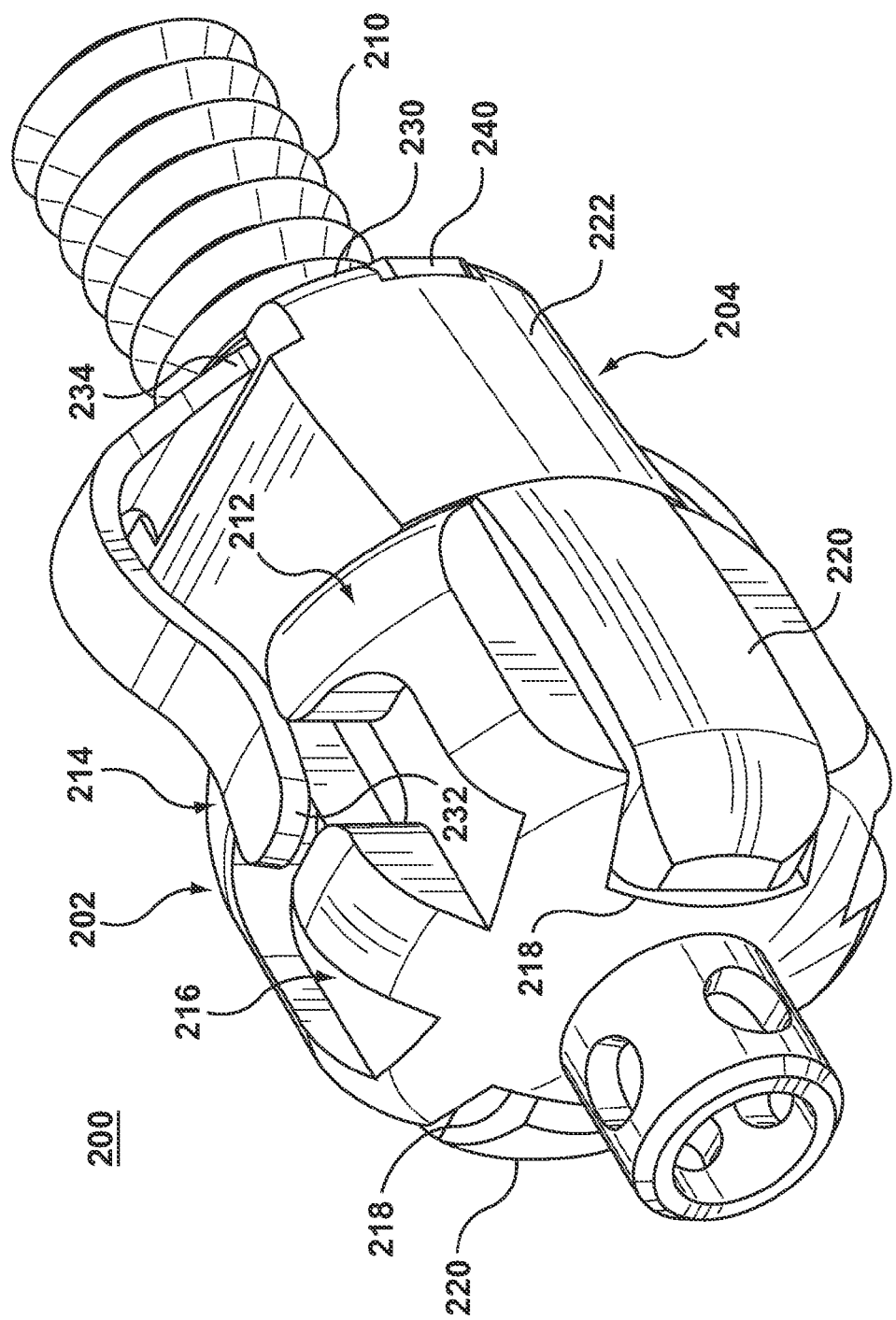

Delivery device 50 of FIG. 3 can be modified so as to include other release features that may assist in the release of a stented prosthetic heart valve from the delivery device 50. Several different features to effectuate release of the valve from the delivery device 50 are discussed below. For example, FIGS. 5A and 5B illustrate an alternative capture assembly 200 that can be used similar to capture assembly 56. Capture assembly 200 includes a spindle 202, an alignment member 204 and a biasing member 206. Spindle 202 is similar to spindle 100 discussed above with regards to FIGS. 4A-4B and generally includes a tubular base 210 and a hub 212 defining a flange 214 and at least one coupling section 216. As with coupling sections 110 shown in FIGS. 4A and 4B, the at least one coupling section 216 form one or more features configured to selectively engage posts 40 of the stented prosthetic heart valve 20. In addition to the coupling section 216, hub 212 further defines longitudinal slots 218 and a tubular extension 219 sized to receive the alignment member 204.

Alignment member 204 includes opposed arms 220 coupled with a main body 222. The arms 220 extend from the body 222 in a generally parallel manner. Upon assembly of spindle 200, body 222 forms an aperture 224 that slides over tubular base 210 and in particular the tubular extension 219 of spindle 202 such that a leading face 226 of body 222 abuts a trailing face 228 of the hub 212. Body 222 also includes a trailing face 229 that forms a number of projections 230 to accommodate the biasing members 206.

Biasing members 206 are similar to biasing members 102 discussed above and define a free end 232, a fixed end 234 and an intermediate region 236. A ring 238 can be formed that interconnects the fixed ends 234 of each of the biasing members 206. The ring 238 further includes opposed tabs 240 that engage face 229 of body 222 and are positioned between respective projections 230. Ring 238 further defines a central aperture 242 that is provided to be positioned over tubular body 210 and tubular extension 219 of spindle 202. In this manner, attachment of capture assembly 200 to shaft 80 can be performed without the need for the use of adhesives to connect ring 238 to shaft 80. In any event, capture assembly 200 operates similar to capture assembly 56 of FIGS. 4A and 4B in effectuating release of a stented prosthetic heart valve from the capture assembly 200.

Figure 6A:
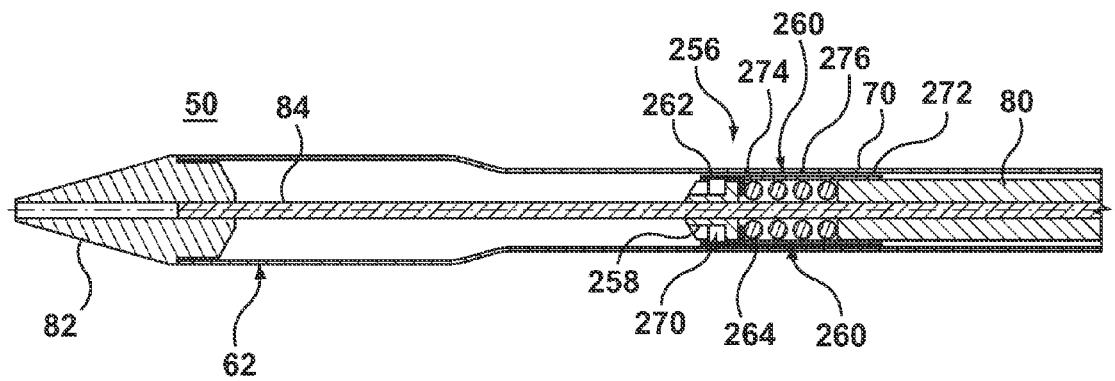
FIGS. 6A-6C are simplified, side views of an alternative capture assembly useful with the delivery device of FIG. 3.
Figure 6B:
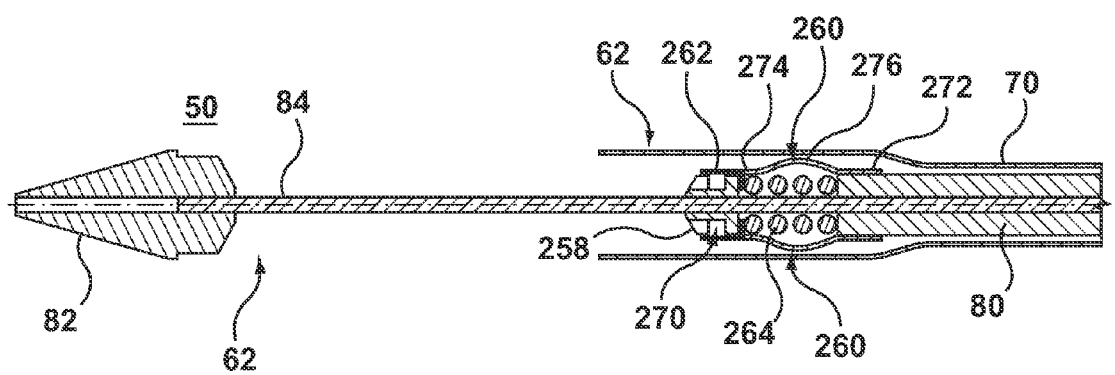
Figure 6C:
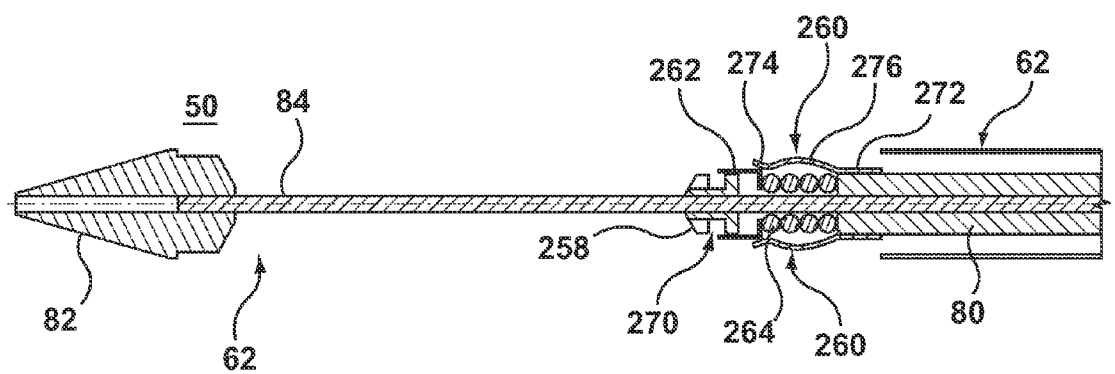

FIGS. 6A-6C illustrate a further embodiment for effectuating release of a stented prosthetic heart valve from a delivery system, and in particular illustrate different stages for release of a stented prosthetic heart valve from delivery system 50. The stented prosthetic heart valve is not illustrated in FIGS. 6A-6C for clarity purposes. In FIGS. 6A-6C, a cross-sectional view of a distal end of delivery device 50 is shown. In particular, the delivery device 50 as illustrated includes the capsule 62, shaft 70, inner support shaft 80, tip 82 and distal segment 84. In FIGS. 6A-6C, an alternative capture assembly 256 is coupled to support shaft 80 and includes a spindle 258, at least one biasing member 260, a coupling member 262, and a release assembly 264.

Spindle 258 is similar to spindles 100 and 202 discussed above, although spindle 258 can be modified in various forms as desired. In general, the spindle 258 includes one or more coupling sections 270 for attachment of the stented prosthetic valve to the spindle 258 and can include one or more clearance features to accommodate the one or more biasing members 260.

The one or more biasing members 260 are configured to transition from a deflected condition as shown in FIG. 6A, to a partially deflected condition as shown in FIG. 6B, and to a normal condition as illustrated in FIG. 6C. In any event, the biasing members 260 are secured to the support shaft 80 at one fixed end 272 and include a free end 274 opposite the support shaft 80. In the embodiment illustrated, the deflected condition of the one or more biasing members 260 deflects the biasing member to a generally linear configuration. In the partially deflected condition of FIG. 6B, the one or more biasing members include an intermediate section 276 that bulges away from the distal segment 84. In the normal condition of FIG. 6C, the one or more biasing members 260 rotate away from the distal segment 84.

The coupling member 262 couples the spindle 258 with the release assembly 264. The coupling member 262 is herein embodied as a collar that is further configured to engage the one or more biasing members 260. The coupling member 262 is configured to cover coupling sections 270 of the spindle 258 so as to secure posts of the stented prosthetic heart valve to the delivery device 50 during delivery. When capsule 62 is partially retracted as illustrated in FIG. 6B, collar 262 is still engaged with the one or more biasing members 260. As also illustrated in FIG. 6B, release assembly 264, herein embodied as a spring member in tension, maintains a similar position to that as illustrated in FIG. 6A. Upon full retraction of the capsule 62 as illustrated in FIG. 6C, the biasing members 260 (an in particular free ends 274) rotate outwardly, allowing the release assembly 264 to pull the coupling member 262 toward the shaft 80. This motion releases the coupling sections 270 of the spindle 258, such that the stented prosthetic valve can be released from the delivery device 50.

Figure 7A:
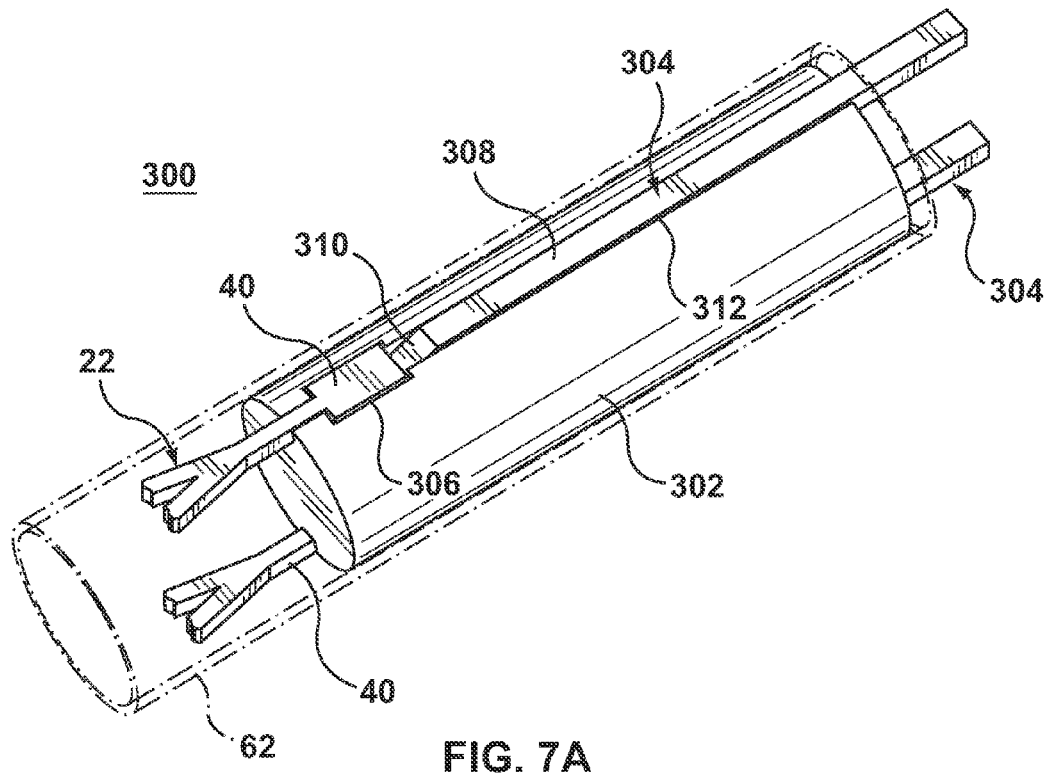
FIGS. 7A-7C are simplified views of an alternative capture assembly useful with the delivery device of FIG. 3.
Figure 7B:
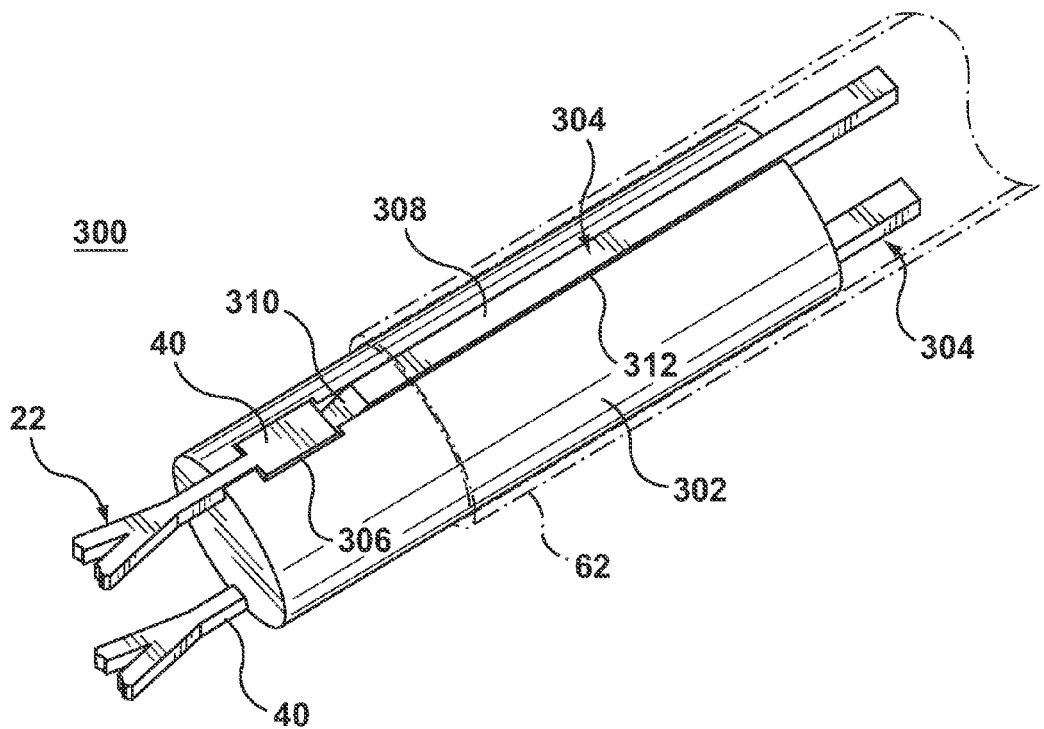
Figure 7C:
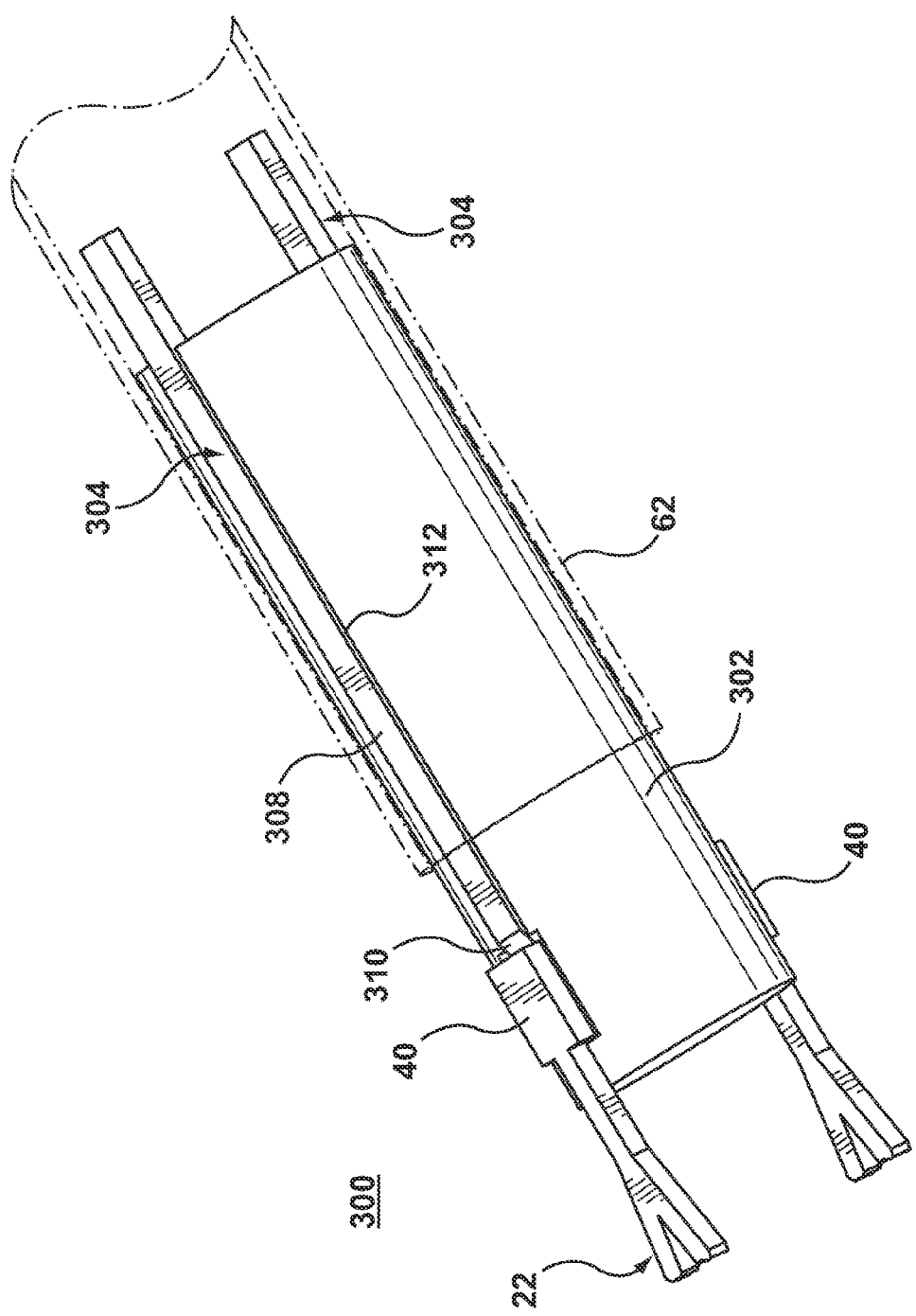

FIGS. 7A-7C illustrates yet another alternative capture assembly 300 that includes a retainer 302 and at least one release bar 304 coupled to the retainer 302 and configured to release a stent frame 22, and in particular posts 40 from one or more coupling sections 306 disposed in the retainer 302. The coupling section 306 defines a recess that receives one or more of the posts 40. In turn, the release bars 304 include an elongate bar member 308 terminating at a tapered or wedged tip 310. The bar members are positioned within an elongate recess 312 provided within the retainer 302 and extend to the handle 58 (FIG. 3) for operation by a suitable actuator positioned on the handle 58. In particular, during deployment of the stent frame 22, the capsule 62 is retracted as illustrated in FIG. 7B. After the capsule 62 has been retracted and as illustrated in FIG. 7C, the release bars 304 are distally advanced, causing the wedged tip 310 to release the posts 40 from retainer 302.

Figure 8A:
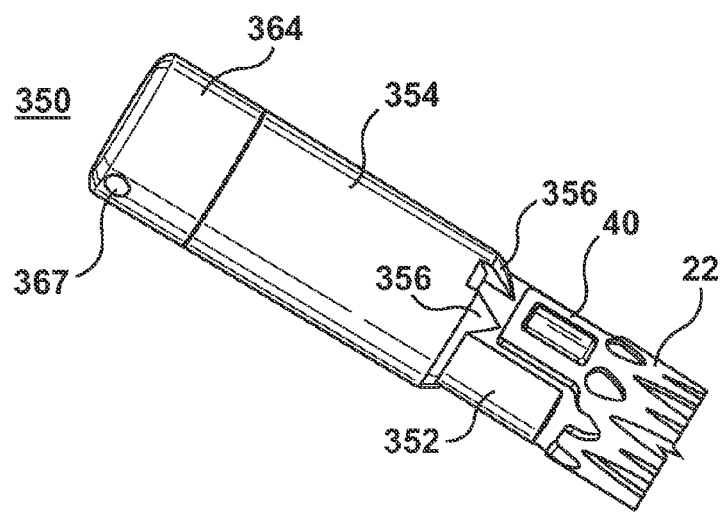
FIGS. 8A-8C are simplified views of an alternative capture assembly useful with the delivery device of FIG. 3.
Figure 8B:
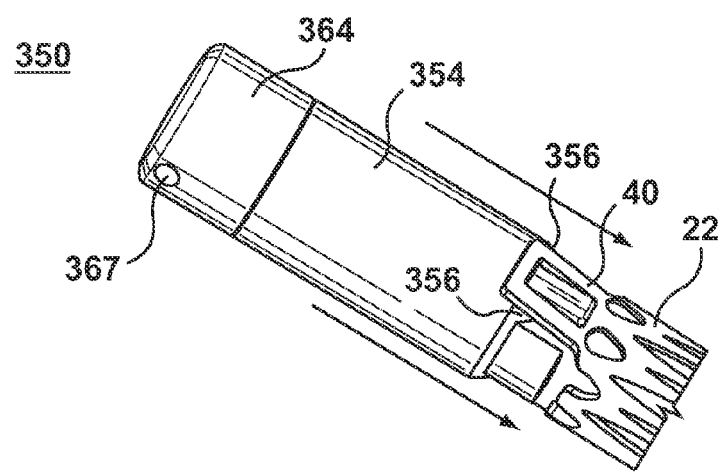
Figure 8C:
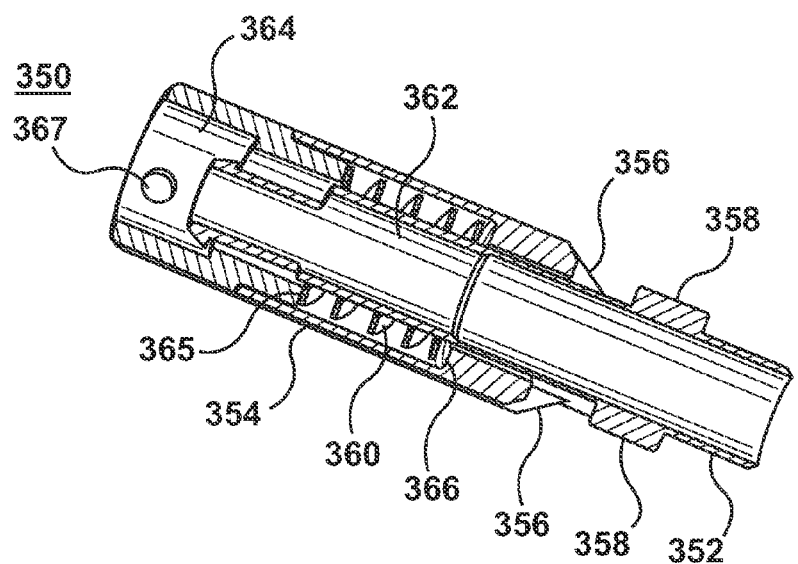

FIGS. 8A-8C illustrate an alternative capture assembly 350. Capture assembly 350 includes an inner hub 352 connected to stent frame 22 and, in particular, a post 40 and a sliding outer hub 354 positioned for relative movement with respect to the inner hub 352. The outer hub is slideable with respect to the inner hub 352 and includes one or more wedged tips 356 that operate to engage a post 40 in order to release the post 40 and stent frame 22 from the capture assembly 350. The inner hub 352 includes one or more protrusions 358 that are provided to capture the post 40 of the stent frame 22. A biasing member 360, herein embodied as a wave spring, is positioned between an inner shaft 362 coupled with the retainer 352 and the outer hub 354. A cap 364 is placed and assembled to the sliding hub 354 such that the biasing element 300 is positioned between the hub 354 and the shaft 362. Moreover, stops 365 and 366 can be positioned on either side of the biasing element 360 to restrain movement of the spring 360. Additionally, cap 364 can include an aperture 367 that can connected to an actuator such as a cable or wire that operates to move outer hub 354 with respect to inner hub 352.

Figure 9A:
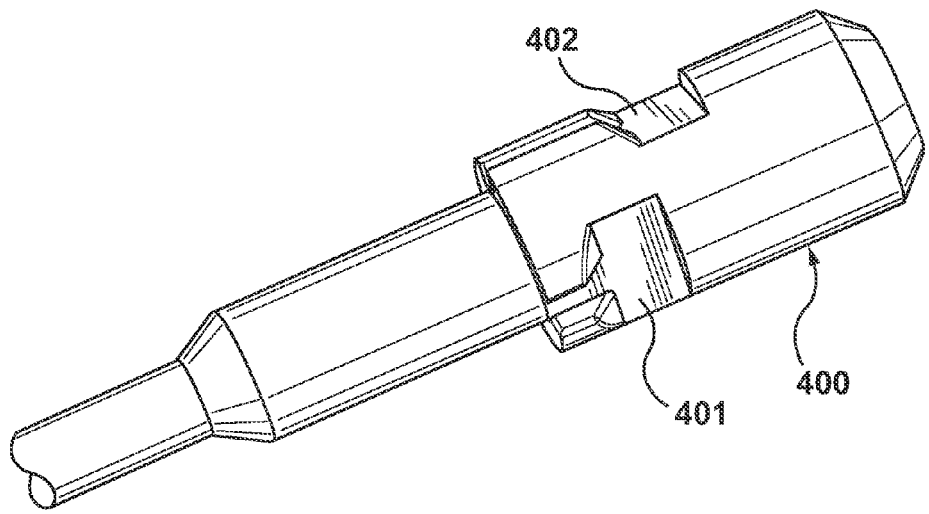
FIGS. 9A and 9B are simplified perspective views of an alternative capture assembly useful with the delivery device of FIG. 3.
Figure 9B:
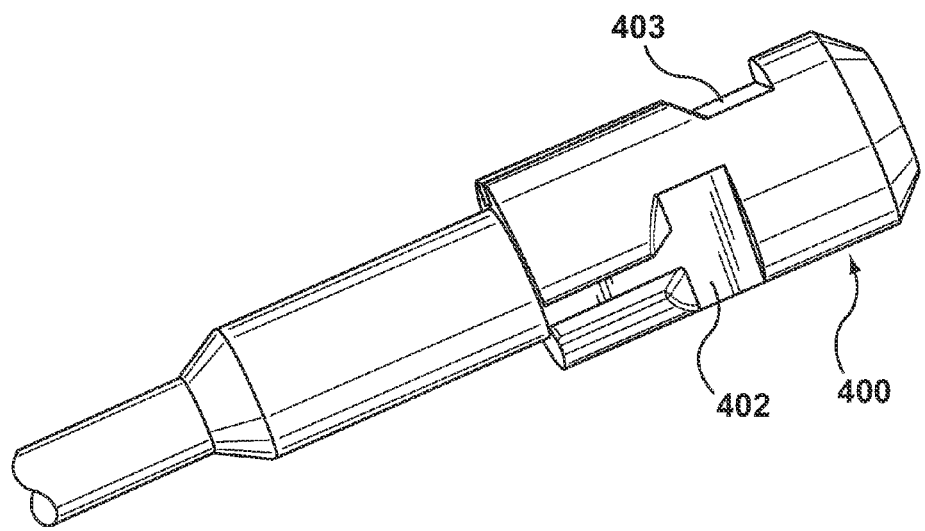
Figure 10:
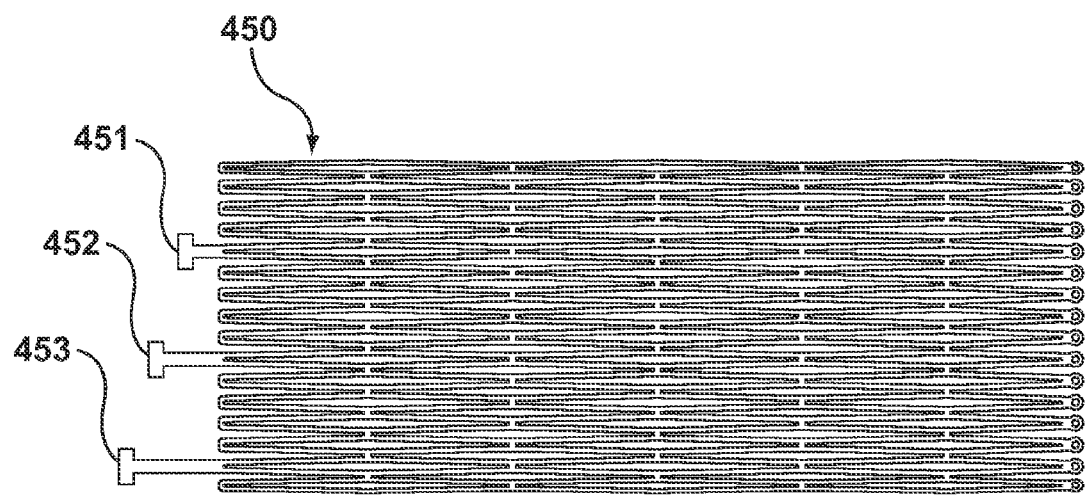
FIG. 10 is a side view of an alternative stent frame.
Figure 11A:
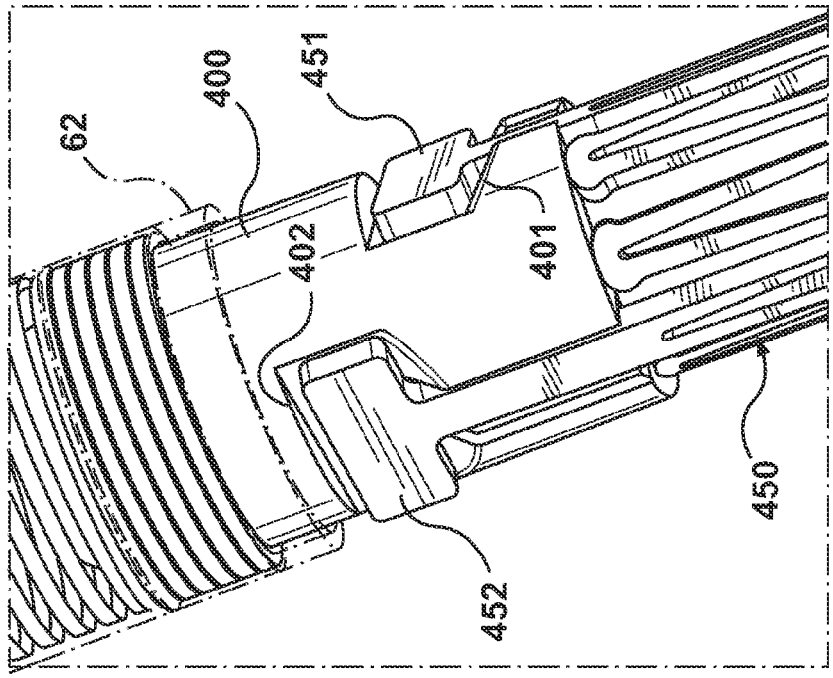
FIGS. 11A and 11B are simplified perspective views of the capture assembly of FIGS. 9A and 9B coupled with the stent frame of FIG. 10.
Figure 11B:
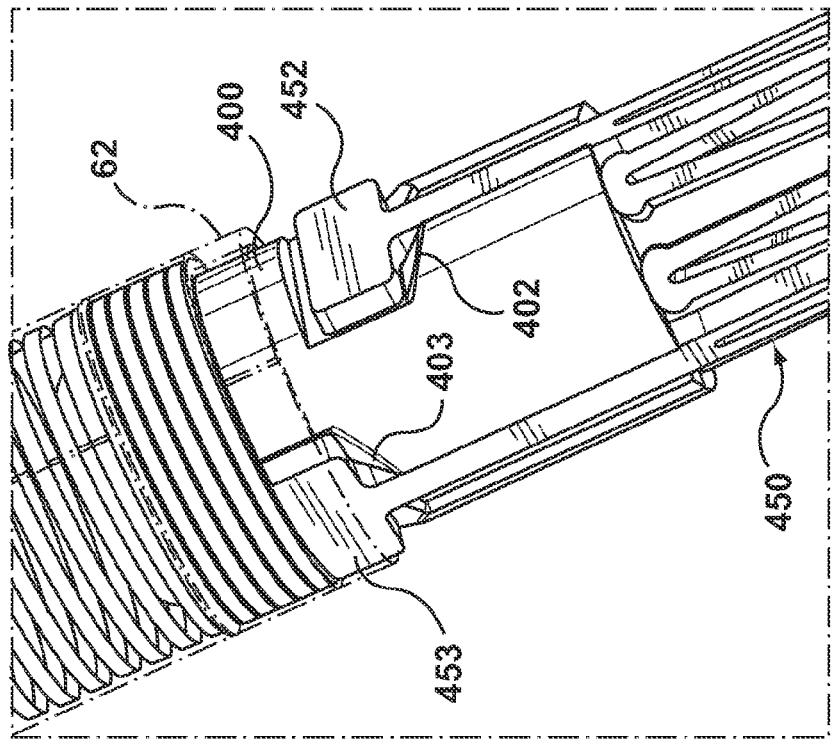

FIGS. 9A and 9B illustrate an alternative capture assembly embodied as a retainer 400 for use with an alternative stent frame 450 as illustrated in FIG. 10. Retainer 400 includes three staggered coupling sections 401, 402 and 403. Each of the staggered coupling sections 401-403 are configured to receive a corresponding post 451, 452 and 453, respectively, of the stent frame 450. Each of the coupling sections 401-403 and post 451-453 are equally spaced about a circumference. In particular, coupling sections 401 through 403 are equally spaced about capture assembly 400 (i.e., with a spacing of 120°). Similarly, posts 451-453 are equally spaced about a circumference of stent frame 450 (also at a spacing of 120°). In one embodiment, post 451 extends about ⅓ the length of post 453 and post 452 extends about ⅔ the length of post 453. In any event, the staggered relationship of the coupling sections 401-403 and posts 451-453 can allow for simplified attachment of the stent frame 450 to the capture assembly 400. In one embodiment, the longest post 453 is positioned within its corresponding coupling section 403. The capsule 62 is then distally advances so as to cover the post 453, as illustrated in FIG. 11A. Next, post 452 can be positioned in its respective coupled section 452 as capsule 62 is further distally advanced. Ultimately, post 451 and stent frame 450 can be covered by capsule 62. During release, capsule 62 is proximally advanced, causing post 451 to be released from capture assembly 400 first, followed by post 452 and post 453. The release of each post assists in releasing subsequent posts from capture assembly 400.

In an alternative embodiment, retainer 400 can be modified to include one or more biasing members that operate to eject posts 451-453 from retainer 400 upon proximal advancement of capsule 62. For example, one biasing member can be provided for each post 451-453, wherein each biasing member extends from a fixed end to a free end, each free end terminating at a different length with respect to its respective fixed end. In this embodiment, each fixed end of the biasing members is positioned at a similar longitudinal position along an inner shaft assembly of a delivery device, where each free end terminates at a different longitudinal position with respect to the other free ends. Moreover, the biasing members can be structurally similar to biasing members 102 illustrated in FIG. 4A with each biasing member having a fixed end, intermediate region and free end. In contrast to biasing members 102 in FIG. 4A, each biasing member terminates at a free end at a different length from ring 148. Alternatively, only one or two biasing members can be provided independent of a number of posts provided on the stent frame 450. In any event, multiple biasing members can have a staggered relationship that corresponds to a respective post in a delivery state of a corresponding delivery device. In the event a single biasing member is used, in one embodiment the single biasing member can be positioned to eject the longest post 453 (i.e., the last post to be released).

The delivery devices and associated release features of the present disclosure provide percutaneous placement of a stented prosthetic heart valve for replacement of an aortic valve, for example. Alternatively, the systems and devices can be used for replacement or repair of other valves and/or in other portions of the body in which a stent is to be implanted. When delivering a valved stent to replace an aortic valve, the delivery devices of the present disclosure can be used with a retrograde delivery approach, for example, although it is contemplated that an antegrade delivery approach can be used, with certain modifications to the delivery device. With the repair systems described herein, full or partial blood flow through the native valve can advantageously be maintained during a period when the valved stent is being deployed into the patient, but is not yet released from its delivery device. This feature can help to prevent complications that may occur when blood flow is stopped or blocked during valve implantation with some other known delivery devices. In addition, it is possible for the clinician to thereby evaluate the opening and closing of leaflets, examine for any paravalvular leakage, and evaluate coronary flow and proper positioning of the prosthetic heart valve within the target anatomy before final release of the stented prosthesis.

The delivery devices shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The devices will further include a delivery catheter, a balloon catheter, and/or a guide wire. A delivery catheter used in this type of delivery device defines a lumen within which the balloon catheter is received. The balloon catheter, in turn, defines a lumen within which the guide wire is slidably disposed. Further, the balloon catheter includes a balloon that is fluidly connected to an inflation source. With the stented valve mounted to the balloon, the transcatheter assembly is delivered through a percutaneous opening in the patient via the delivery device. Once the stented prosthetic heart valve is properly positioned, the balloon catheter is operated to inflate the balloon, thus transitioning the stented prosthesis to an expanded arrangement.

The systems, devices, and methods of the present disclosure provide a marked improvement over previous designs. The delivery device is configured so that the stent frame of the stented prosthetic heart valve will release from the delivery device at a pre-designated step of the delivery sequence. These delivery devices thereby advantageously allow the clinician to entirely remove an outer sheath from a valved stent prior to releasing the stent from the delivery device. In addition, the systems of the present disclosure allow the inflow region and at least a portion of the outflow region of the valved stent to open or release so that the valve structure function can be determined prior to final release of the stented valve. The disclosed capture assembly provides a simplified design that better ensures consistent deployment, as well as promotes use with optional T-like shaped posts of the prosthetic heart valve stent frame to permit open assessment prior to full deployment.

Although the present disclosure has been described with reference to preferred embodiments, workers skilled in the art will recognize that changes can be made in form and detail without departing from the spirit and scope of the present disclosure.

What is claimed is:

1. A delivery device for percutaneously deploying a stented prosthetic heart valve including a stent frame to which a valve structure is attached, the device comprising:
   a delivery sheath assembly terminating at a distal end and defining a lumen;
   an inner shaft slidably disposed within the lumen; and
   a capture assembly for selectively coupling the stented prosthetic heart valve relative to the inner shaft, the capture assembly comprising:
      a spindle attached to the inner shaft and including at least one coupling section defining a slot; and
      a biasing member positioned in the slot and configured to transition from a deflected condition to a normal condition, wherein the biasing member includes a fixed end and a free end rotatable about the fixed end, a radial projection of the free end relative to a centerline of the inner shaft is greater in the normal condition than in the deflected condition,
   wherein the delivery device is configured to provide:
      a delivery state in which the delivery sheath assembly retains the stented prosthetic heart valve over the inner shaft and the biasing member in the deflected condition, including a portion of the stented prosthetic heart valve engaged with the at least one coupling section and the biasing member forced to the deflected condition; and
      a deployment state in which the distal end of the delivery sheath assembly is withdrawn from covering at least a portion of the capture assembly, wherein the biasing member transitions to the normal condition such that the free end rotates about the fixed end to radially deflect the stent frame, and wherein the biasing member further includes an intermediate region positioned between the free end and the fixed end, wherein the intermediate region projects radially to a greater distance from the centerline than the fixed end in the normal and deflected conditions.

2. The device of claim 1, wherein the spindle includes two coupling sections and wherein the capture assembly includes two biasing members positioned within the two coupling sections.

3. The device of claim 1, wherein the intermediate region forms a hump between the fixed end and the free end.

4. The device of claim 1, wherein a post of the stented prosthetic heart valve is positioned between the biasing member and the outer sheath assembly when the device is in the delivery state.

5. The device of claim 1, further comprising:
   an alignment member selectively coupled with the spindle, the alignment member including features to align the spindle with the biasing member.

6. The device of claim 1, further comprising:
   a coupling member comprising a spring member positioned between the shaft and the spindle and wherein, in transition from the delivery state to the deployment state, the coupling member moves relative to the at least one coupling section and releases the biasing member from the at least one coupling section.

7. The device of claim 1, wherein the capture assembly includes multiple biasing members connected together at respective fixed ends to a ring, the biasing members positioned with respect to one another in a staggered relationship such that each biasing member extends from the ring and terminates at a free end at a different length from the ring.

8. A system for restoring a defective heart valve of a patient, the system comprising:
   a prosthetic heart valve having a stent frame and a valve structure attached to the stent frame, the stent frame defining a distal region and a proximal region, the proximal region forming at least one post; and
   a delivery device, comprising:
      a delivery sheath assembly terminating at a distal end and defining a lumen;
      an inner shaft slidably disposed within the lumen; and
      a capture assembly for selectively coupling the prosthetic heart valve relative to the inner shaft, the capture assembly comprising:
         a spindle attached to the inner shaft and including at least one coupling section defining a slot; and
         a biasing member positioned in the slot and configured to transition from a deflected condition to a normal condition, wherein the biasing member includes a fixed end and a free end rotatable about the fixed end, a radial projection of the free end relative to a centerline of the inner shaft is greater in the normal condition than in the deflected condition,
   wherein the delivery device is configured to provide:
      a delivery state in which the delivery sheath assembly retains the prosthetic heart valve over the inner shaft and the biasing member in the deflected condition, including a portion of the prosthetic heart valve engaged with the at least one coupling section and the biasing member forced to the deflected condition; and
      a deployment state in which the distal end of the delivery sheath assembly is withdrawn from covering at least a portion of the capture assembly, wherein the biasing member transitions to the normal condition such that the free end rotates about the fixed end to radially deflect the stent frame, and wherein the biasing member further includes an intermediate region positioned between the free end and the fixed end, wherein the intermediate region projects radially to a greater distance from the centerline than the fixed end in the normal and deflected conditions.

9. The system of claim 8, wherein the spindle includes two coupling sections and wherein the capture assembly includes two biasing members positioned within the two coupling sections.

10. The system of claim 8, wherein the intermediate region forms a hump between the fixed end and the free end.

11. The system of claim 8, wherein the at least one post of the prosthetic heart valve is positioned between the biasing member and the outer sheath assembly when the device is in the delivery state.

12. The system of claim 8, further comprising:
an alignment member selectively coupled with the spindle, the alignment member including features to align the spindle with the biasing member.

13. The system of claim 8, further comprising:
a coupling member comprising a spring member positioned between the shaft and the spindle and wherein, in transition from the delivery state to the deployment state, the coupling member moves relative to the at least one coupling section and releases the biasing member from the at least one coupling section.

14. The system of claim 8, wherein the capture assembly includes multiple biasing members connected together at respective fixed ends to a ring, the biasing members positioned with respect to one another in a staggered relationship such that each biasing member extends from the ring and terminates at a free end at a different length from the ring.

* * * * *